(12) United States Patent
Biedermann et al.

(10) Patent No.: US 9,517,092 B2
(45) Date of Patent: Dec. 13, 2016

(54) INSTRUMENT FOR ASSEMBLING A POLYAXIAL BONE ANCHOR

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weiswell (DE); Bernd Fischer, Braünlingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 104 days.

(21) Appl. No.: 14/049,099

(22) Filed: Oct. 8, 2013

(65) Prior Publication Data

US 2014/0107708 A1    Apr. 17, 2014

Related U.S. Application Data

(60) Provisional application No. 61/711,349, filed on Oct. 9, 2012.

(30) Foreign Application Priority Data

Oct. 9, 2012 (EP) .................................... 12187754

(51) Int. Cl.
*A61B 17/70* (2006.01)
*A61B 17/88* (2006.01)

(52) U.S. Cl.
CPC ....... *A61B 17/7082* (2013.01); *A61B 17/7037* (2013.01); *A61B 17/7076* (2013.01);
(Continued)

(58) Field of Classification Search
CPC ........ A61B 17/7032–17/7043; A61B 17/7074;
A61B 17/7076; A61B 17/7082; A61B
2019/4836; A61B 2019/4842; A61B
2019/4857; A61B 2019/4863; A61B
2019/461; A61B 2019/462; A61B 19/46
See application file for complete search history.

(56) References Cited

U.S. PATENT DOCUMENTS 1,459,896 A * 6/1923 John ............................... 33/544
2,654,156 A * 10/1953 Boyer ............................. 33/836
(Continued)

FOREIGN PATENT DOCUMENTS

CN        100998517 A      7/2007
WO    WO 2011/043799 A1    4/2011

OTHER PUBLICATIONS

European Search Report and Opinion issued by the EPO for EP 12187754.2 on Mar. 15, 2013, 9 pages.
(Continued)

*Primary Examiner* — Jacqueline Johanas
(74) *Attorney, Agent, or Firm* — Lewis Roca Rothgerber Christie LLP

(57) ABSTRACT

An instrument for assembling a polyaxial bone anchor is provided, the polyaxial bone anchor including a bone anchoring element and a receiving part that is configured to pivotably receive the bone anchoring element wherein the instrument includes a first member that is configured to engage the receiving part, a second member that is configured to contact the anchoring element when it is received in the receiving part, and a position indicator that is configured to indicate the position of the anchoring element relative to the receiving part based on the position of the second member relative to the first member.

22 Claims, 13 Drawing Sheets

(52) U.S. Cl.
CPC ............. *A61B 90/92* (2016.02); *A61B 90/94* (2016.02); *A61B 2090/067* (2016.02); *A61B 2090/0808* (2016.02)

(56) References Cited

U.S. PATENT DOCUMENTS

| | | | |
|---|---|---|---|
| 2,689,408 A * | 9/1954 | Cornell et al. ................. 33/544 |
| 2,893,130 A * | 7/1959 | Ierokomos .................... 33/544 |
| 5,870,835 A * | 2/1999 | Stieff ............................ 33/600 |
| 5,928,243 A * | 7/1999 | Guyer ........................... 606/102 |
| 6,063,090 A | 5/2000 | Schläpfer |
| 7,762,005 B2 * | 7/2010 | Pelotte .......................... 33/836 |
| 8,034,089 B2 | 10/2011 | Matthis et al. |
| 8,221,427 B2 * | 7/2012 | Roh ............................ 606/86 A |
| 8,257,409 B2 * | 9/2012 | Schlienger ......... A61B 17/1703 606/329 |
| 8,870,891 B2 * | 10/2014 | Lizardi et al. ................ 606/102 |
| 8,959,989 B2 * | 2/2015 | McNaught ..................... 73/146 |
| 8,979,848 B2 * | 3/2015 | Butters et al. ............. 606/86 A |
| 2005/0228400 A1 | 10/2005 | Chao et al. |
| 2007/0043378 A1 | 2/2007 | Kumar et al. |
| 2007/0233086 A1 | 10/2007 | Harms et al. |
| 2008/0200918 A1 | 8/2008 | Spitler et al. |
| 2008/0312702 A1 * | 12/2008 | Schlienger ......... A61B 17/1703 606/329 |
| 2009/0320310 A1 * | 12/2009 | Pelotte ........................... 33/836 |
| 2010/0114108 A1 * | 5/2010 | Strauss ......................... 606/102 |
| 2010/0121330 A1 * | 5/2010 | Parmigiani .................... 606/79 |
| 2010/0204735 A1 | 8/2010 | Gephart et al. |
| 2010/0305625 A1 | 12/2010 | Kuntz et al. |
| 2011/0000344 A1 * | 1/2011 | Summers ....................... 81/429 |
| 2011/0004256 A1 * | 1/2011 | Biedermann et al. ........ 606/301 |
| 2011/0124813 A1 | 5/2011 | Casalini et al. |
| 2012/0031792 A1 | 2/2012 | Petit |
| 2012/0124813 A1 | 5/2012 | Biedermann et al. |
| 2012/0130387 A1 | 5/2012 | Simpson et al. |
| 2012/0203237 A1 * | 8/2012 | Bryan et al. ................ 606/102 |
| 2012/0330323 A1 * | 12/2012 | Lizardi et al. .............. 606/102 |
| 2015/0005878 A1 * | 1/2015 | Lizardi et al. ............. 623/13.12 |

OTHER PUBLICATIONS

CN Office action for Application No. 201310447330.0 dated Aug. 16, 2016 and English translation (15 pages).

* cited by examiner

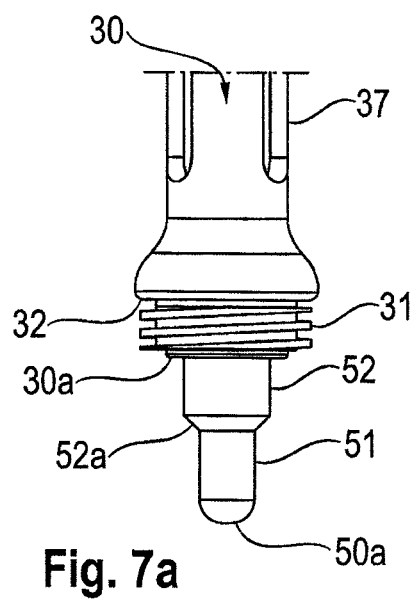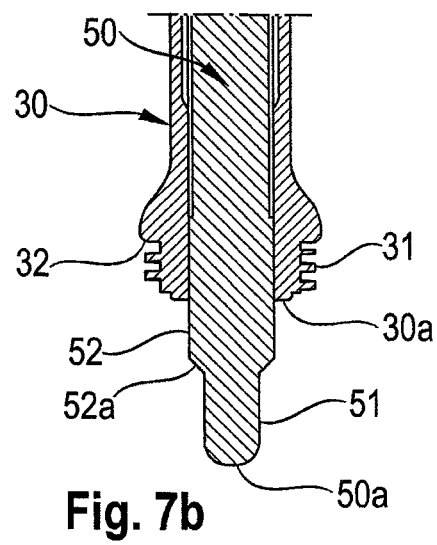
Fig. 7a
Fig. 7b
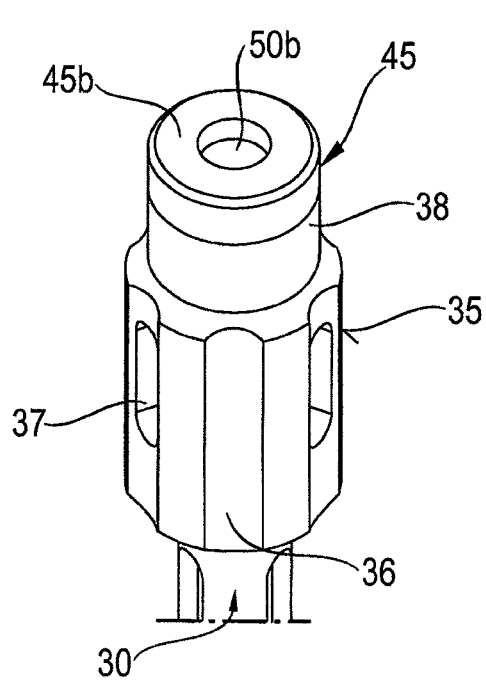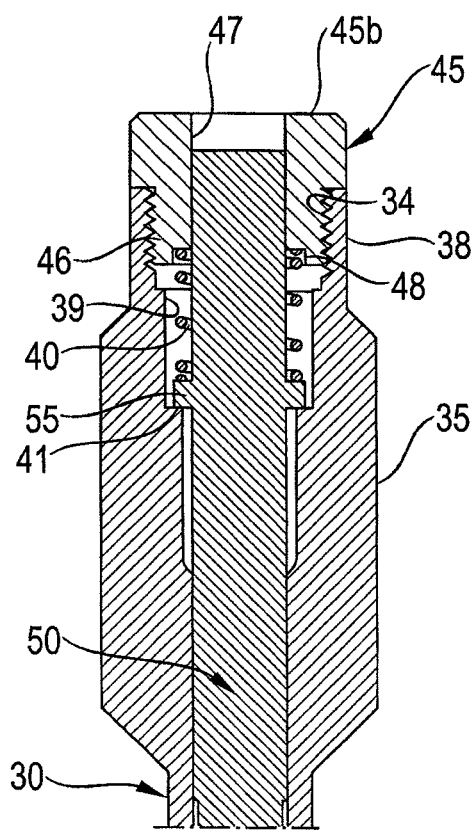
Fig. 8a
Fig. 8b

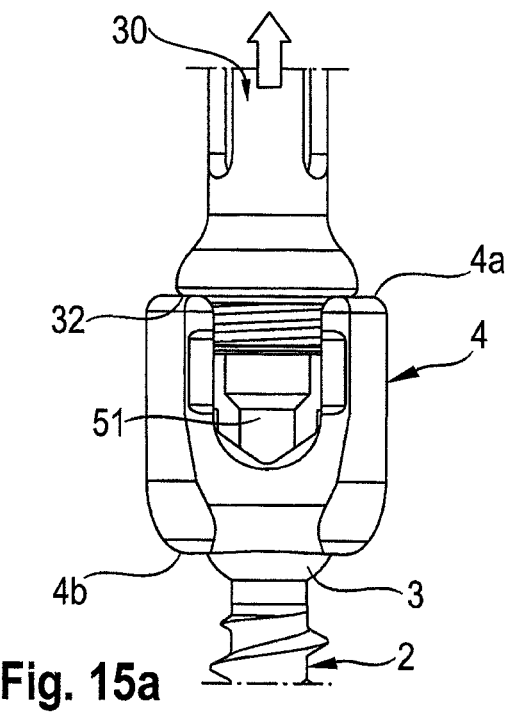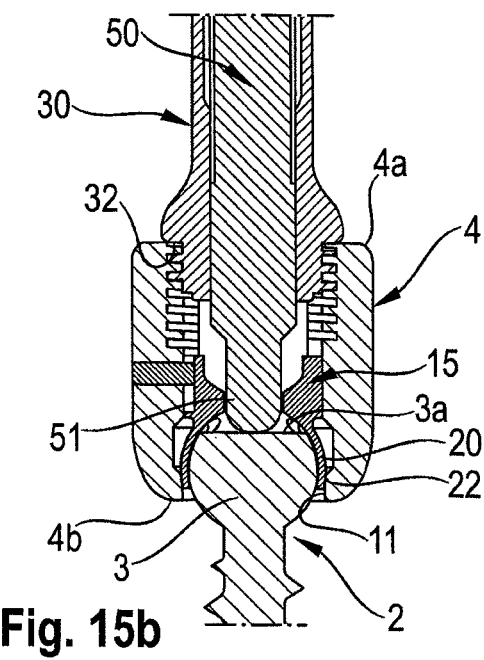
Fig. 15a  Fig. 15b
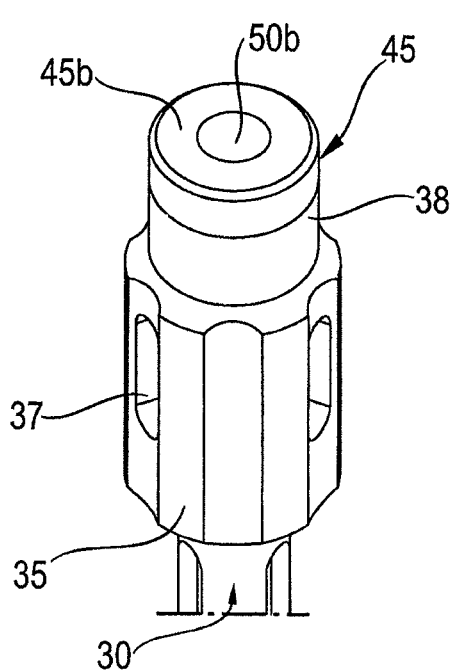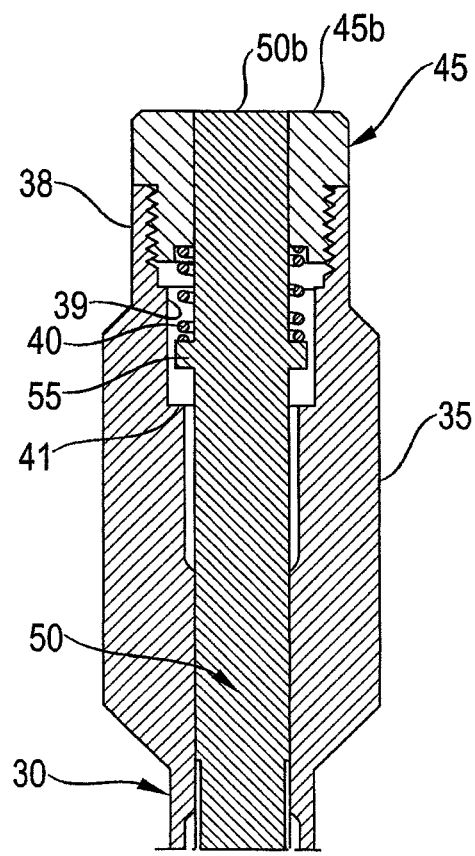
Fig. 16a  Fig. 16b

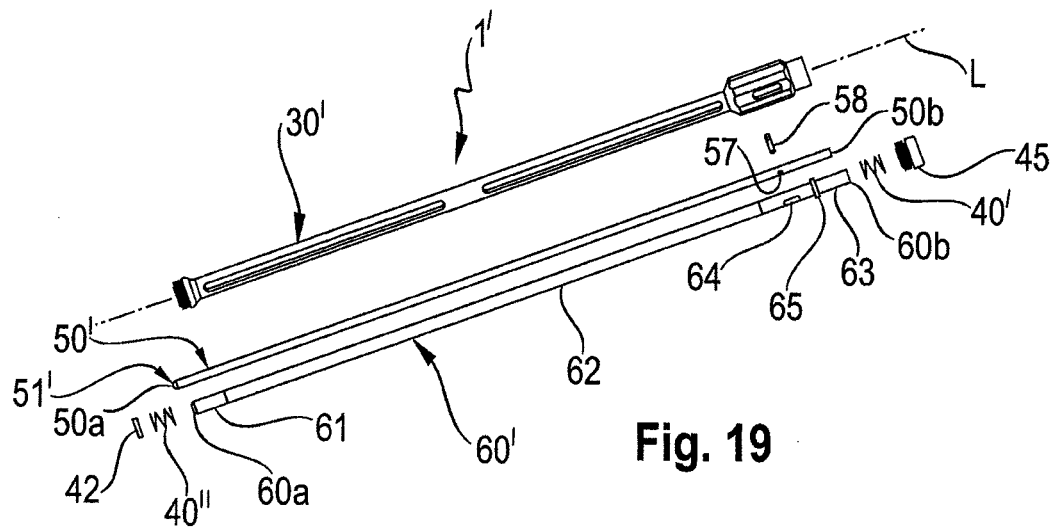
Fig. 19
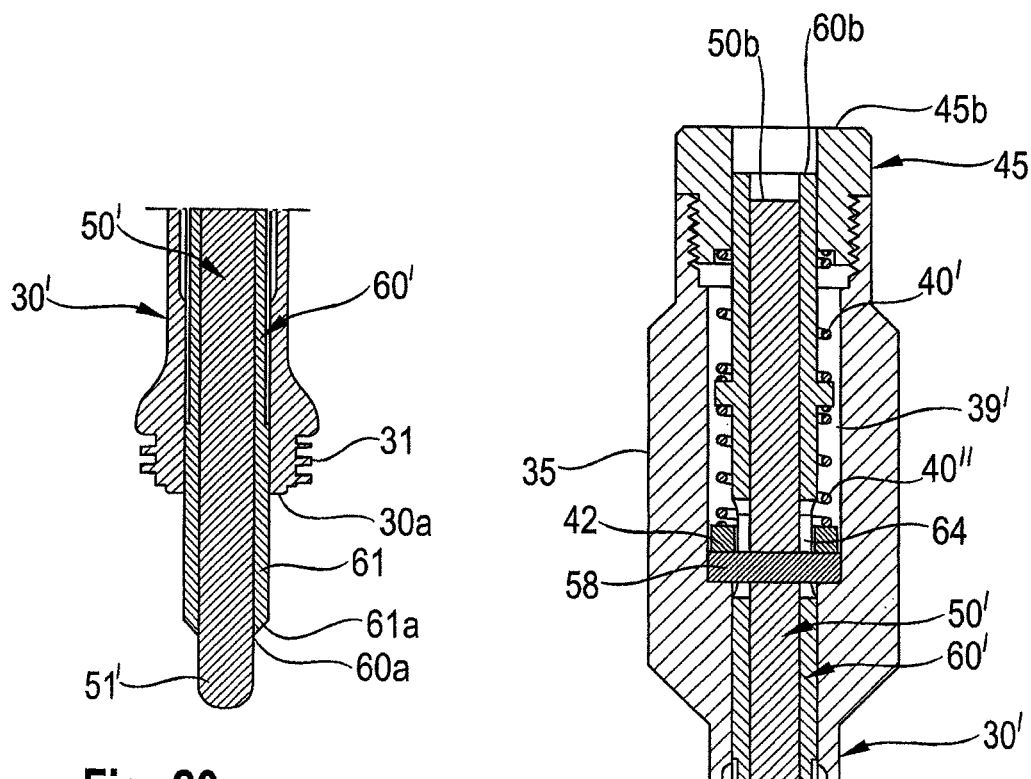
Fig. 20a
Fig. 20b

INSTRUMENT FOR ASSEMBLING A POLYAXIAL BONE ANCHOR

CROSS-REFERENCE TO RELATED APPLICATIONS

The present disclosure claims the benefit of U.S. Provisional Patent Application Ser. No. 61/711,349, filed Oct. 9, 2012, the contents of which are hereby incorporated by reference in their entirety, and claims priority from European Patent Application EP 12 187 754.2, filed Oct. 9, 2012, the contents of which are hereby incorporated by reference in their entirety.

BACKGROUND

Field of the Invention

The invention relates to an instrument for assembling a polyaxial bone anchor. A polyaxial bone anchor typically includes a bone anchoring element and a receiving part that is configured to pivotably receive the bone anchoring element. The angular position of the bone anchoring element relative to the receiving part can be locked by exerting pressure onto a head of the bone anchoring element. The instrument includes a first member configured to engage the receiving part and a second member configured to contact the bone anchoring element and a position indicator that indicates the position of the bone anchoring element relative to the receiving part. The instrument is particularly suitable for the in situ assembly of a bottom loading polyaxial bone anchor.

Description of Related Art

A tool for assembling a polyaxial bone anchor is known, for example, from US 2012/0124813 A1. The polyaxial bone anchor is a bottom loading polyaxial bone anchor that comprises an outer locking ring configured to be positioned around a head receiving portion of the receiving part and to exert pressure onto the head of the bone anchoring element. With the tool, the bone anchoring element and the head receiving part with the locking ring can be assembled before the bone anchor is inserted into a bone part or a vertebra.

Other bottom loading polyaxial bone anchors are known that comprise an inner compression member to exert pressure onto the head of the bone anchoring element. Such bottom loading polyaxial bone anchors that allow for in situ assembly, i.e. inserting the bone anchoring element into the bone first and thereafter assembling the receiving part with the head of the bone anchoring element, are known, for example, from U.S. Pat. No. 6,063,090 or from U.S. Pat. No. 8,034,089 B2. In the case of in situ mounting of the receiving part onto the head of the anchoring element, in certain situations it might be difficult to recognize whether the receiving part has been correctly mounted onto the bone anchoring element.

SUMMARY

It is an object of the invention to provide an instrument for assembling a polyaxial bone anchor, and, in a preferred embodiment, for the in situ assembly of a bottom loading polyaxial bone anchor. It is a further object to provide a system of a polyaxial bone anchor and such an instrument.

In one embodiment, the instrument provides for an indication of the position of the head of the bone anchoring element relative to the receiving part. Hence, the surgeon or any other personnel assisting him obtains feedback as to whether the receiving part is mounted correctly onto the head of the bone anchoring element. This increases the safety of the assembling step and the reliability of the bone anchor.

In a further embodiment, the instrument may provide an additional indication of the position of a pressure element that is arranged in the receiving part and that serves to lock the position of the bone anchoring element relative to the receiving part. This further increases the safety of the polyaxial bone anchor when it is assembled.

The instrument can be provided with a mechanism for indicating the relative position of the receiving part and the bone anchoring element. The instrument may also include sensors, switches or other detection means that detect the position of the bone anchoring element relative to the receiving part or of the pressure element relative to the receiving part. The position indicator may include visible indication means based on the position of mechanical parts and/or may include electro-optical indication means, such as LED's and/or acoustic indication means. Visible marks, such as height differences between a caliper and a housing and colors can be easily recognized during surgery and therefore facilitate the procedure.

BRIEF DESCRIPTION OF THE DRAWINGS

Further features and advantages will become apparent from and will be best understood by reference to the following detailed description reviewed in conjunction with the accompanying drawings. In the drawings:

FIG. 7a shows a side view of a front end portion of the instrument according to the first embodiment.

FIG. 7b shows a cross-sectional view of the portion shown in FIG. 7a.

FIG. 8a shows a perspective view of the rear end portion of the instrument according to the first embodiment.

FIG. 8b shows a cross-sectional view of the portion shown in FIG. 8a.

FIG. 9b shows a cross-sectional view of the portion shown in FIG. 9a.

FIG. 10a shows a perspective view of the rear end portion of the instrument attached to the receiving part as shown in FIG. 9a.

FIG. 10b shows a cross-sectional view of the portion shown in FIG. 10a.

FIG. 11b shows a cross-sectional view of the portion shown in FIG. 11a.

FIG. 12a shows a perspective view of the rear end portion of the instrument in the state of FIG. 11a.

FIG. 12b shows a cross-sectional view of the portion shown in FIG. 12a.

FIG. 13b shows a cross-sectional view of the portion shown in FIG. 13a.

FIG. 14a shows a perspective view of the rear end portion of the instrument in the state shown in FIG. 13a.

FIG. 14b shows a cross-sectional view of the portion shown in FIG. 14a.

FIG. 15a shows a side view of the front end portion of the instrument attached to the receiving part in which the bone anchoring element is clamped in the receiving part according to the first embodiment.

FIG. 15b shows a cross-sectional view of the portion shown in FIG. 15a.

FIG. 16a shows a perspective view of the rear end portion of the instrument in a state shown in FIG. 15a.

FIG. 16b shows a cross-sectional view of the portion shown in FIG. 16a.

FIG. 17b shows a cross-sectional view of the portion shown in FIG. 17a.

FIG. 18a shows a perspective view of the rear end portion of the instrument in a state shown in FIG. 17a.

FIG. 18b shows a cross-sectional view of the portion shown in FIG. 18a.

FIG. 19 shows a perspective exploded view of the instrument according to a second embodiment.

FIG. 20a shows a cross-sectional view of the front end portion of the instrument according to the second embodiment.

FIG. 20b shows a cross-sectional view of the rear end portion of the instrument of FIG. 19.

FIG. 21b shows a cross-sectional view of the rear end portion of the instrument in the state shown in FIG. 21a.

FIG. 22b shows a cross-sectional view of the rear end portion of the instrument in the state shown in FIG. 22a.

FIG. 23b shows a cross-sectional view of the rear end portion of the instrument in the state shown in FIG. 23a.

FIG. 24b shows a cross-sectional view of the rear end portion of the instrument in a state shown in FIG. 24a.

FIG. 25a shows a cross-sectional view of the front end portion of the instrument attached to the receiving part in a state where the head of the bone anchoring has been pivoted to one side and clamped according to the second embodiment.

FIG. 25b shows a cross-sectional view of the rear end portion of the instrument in a state shown in FIG. 25a.

FIG. 25c shows a perspective view of the rear end portion of the instrument in a state shown in FIG. 25a.

DETAILED DESCRIPTION

Figure 1:
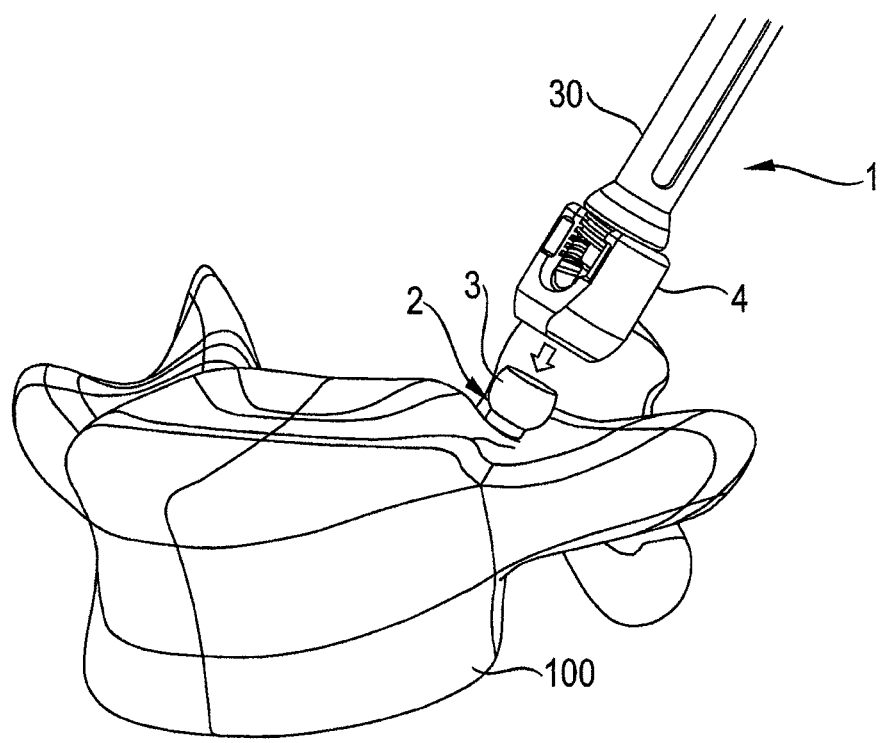
FIG. 1 shows a perspective view of a step of in situ assembly of the receiving part of a polyaxial bone anchor and a bone anchoring element using the tool according to a first embodiment.

Referring to FIG. 1, an instrument 1 according to a first embodiment is attached to a receiving part 4 that is to be mounted to a bone anchoring element 2. The bone anchoring element 2 has been inserted beforehand into the pedicle of a vertebra 100. As further shown in FIG. 2, the bone anchoring element 2 comprises a threaded shank 2a for anchoring into a bone or vertebra and a head 3 that typically has a circular segment-shape and a free end surface 3a on the side opposite to the shank 2a. The receiving part 4 comprises a top end 4a and the bottom end 4b opposite the top end and a central axis C passing through the top end 4a and the bottom end 4b. A bore 5 is provided which is coaxial with the axis of symmetry. In a first region adjacent to the top end 4a, the receiving part 4 has a substantially U-shaped recess 6 that is symmetric with respect to the central axis C, the recess 6 having a bottom directed towards the bottom end 4b and two lateral legs 7a, 7b extending towards the top end 4a. A channel formed by the substantially U-shaped recess 6 is sized so as to receive a rod 101 therein, the rod 101 being provided to connect a plurality of bone anchors. In the region of the legs 7a, 7b an internal thread 8 which cooperates with an inner screw 9, is provided. The inner screw 9 serves as a fixation element that is configured to fix the rod 101 in the U-shaped recess 6.

Figure 9A:
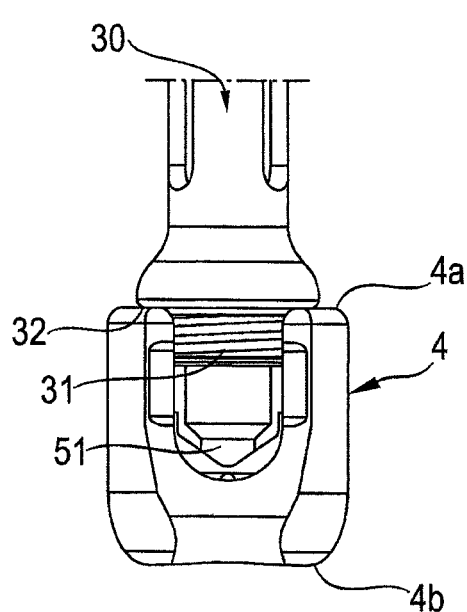
FIG. 9a shows a side view of the front end portion of the instrument attached to the receiving part according to the first embodiment.
Figure 9B:
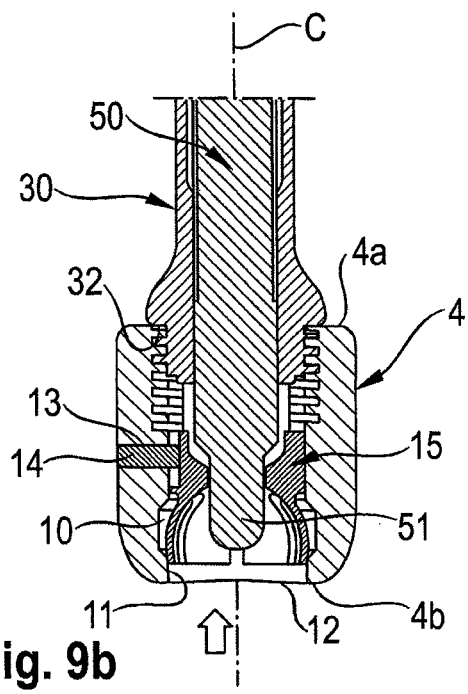

As can be seen, for example, in FIG. 9b, the receiving part 4 further comprises a hollow substantially cylindrical widened region 10 adjacent to the bore 5 with an inner diameter that is greater than the inner diameter of the bore 5. At a second region near the bottom end 4b, the widened cylindrical region 10 is followed by a tapered portion 11 tapering towards bottom end 4b with a cone angle. An opening 12 is provided at the bottom end 4b, a diameter of which is larger than a diameter of the head 3 so that the head 3 can be inserted in the receiving part 4 from the bottom end 4b.

Figure 2:
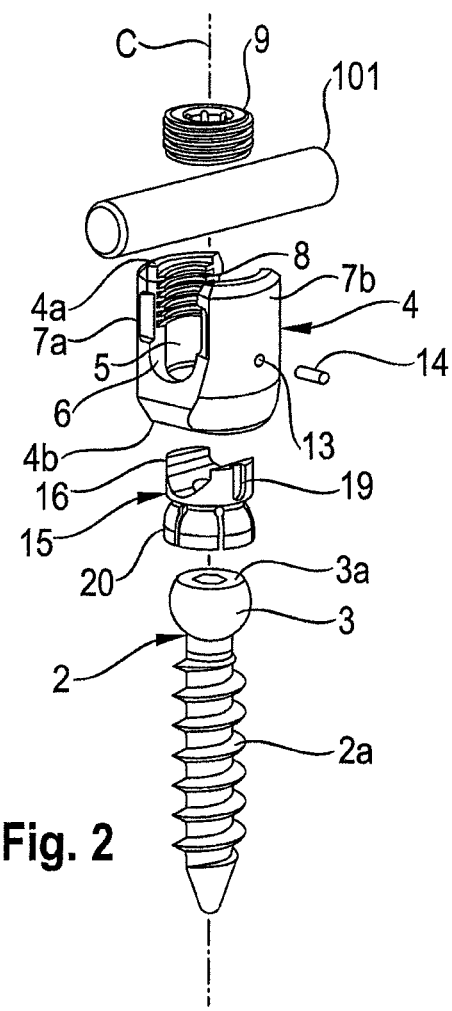
FIG. 2 shows a perspective exploded view of an example of a polyaxial bone anchor.

Referring to FIG. 2, on one of the legs 7b, a substantially transverse bore 13 is provided for receiving a pin 14. The bore 13 may be located substantially at a center of the leg 7b in circumferential direction.

Figure 3:
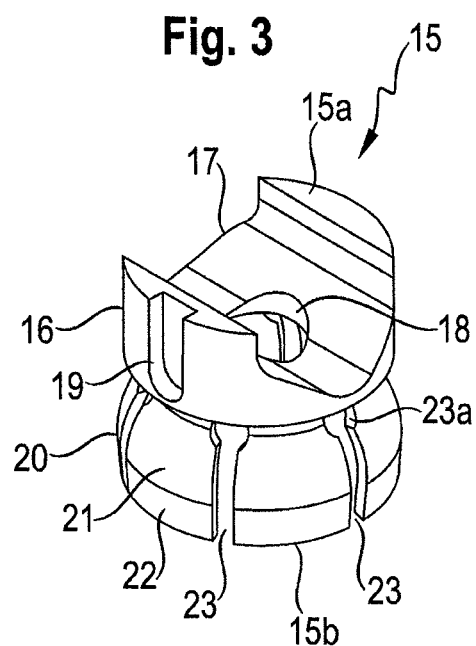
FIG. 3 shows a perspective view of the top of the pressure element of the polyaxial bone anchor of FIG. 2.
Figure 4:
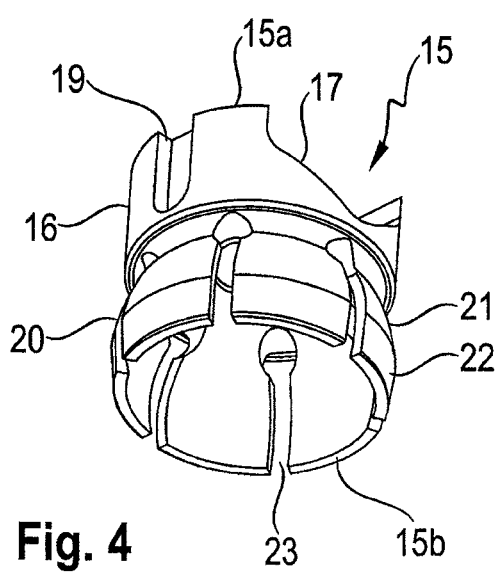
FIG. 4 shows a perspective view of the bottom of the pressure element of FIG. 3.

Referring in particular to FIGS. 2 to 4, the polyaxial bone anchor further includes a pressure element 15 having a top end 15a and an opposite bottom end 15b. Adjacent to the top end 15a, a substantially cylindrical section 16 is provided with an outer diameter that is slightly smaller than the inner diameter of the bore 5 such that the pressure element 15 can slide within the bore 5. A substantially V-shaped recess 17 is provided adjacent to the top end 15a that has a rounded bottom and that serves for accommodating and supporting the rod 101 therein. With the substantially V-shaped cross-section, rods with different diameters can be placed into the recess 17 and supported therein. Furthermore, a coaxial bore 18 is provided at the bottom of the V-shaped recess 17. At one of the side walls provided by the V-shaped recess 17, an elongate recess 19 extending substantially parallel to the central axis C and being open on the top end 15a is provided. The elongate recess 19 is sized so as to receive a front end portion of the pin 14 therein. In addition, the recess 19 is closed towards the bottom end 15b thereby establishing a stop for the pin 14 during an upward movement of the pressure element 15 in the receiving part 4.

The pressure element 15 further comprises a cap-like portion 20 that is hollow inside and has a substantially spherical first exterior surface portion 21 adjacent to the cylindrical portion 16 and a tapered exterior surface portion 22 tapering towards the bottom end 15b that cooperates with the tapered portion 11 of the receiving part 4. A plurality of slits 23 that are open to the bottom end 15b and that extend through the wall of the cap-like portion 20 are provided in order to make the cap-like portion 20 flexible. The slits may have circular or otherwise widened end sections 23a near to the cylindrical portion 16 of the pressure element 15, as shown in FIG. 3. The cap-like portion 20 of the pressure element is shaped and sized such that it mates with the exterior surface of the head 3 of the bone anchoring element 2 when the cap-like portion 20 is placed onto the head 3. A maximum outer diameter of the cap-like portion 20 is slightly greater than an inner diameter of the lower opening 12 of the receiving part 4, such that the pressure element can not fall out through the lower opening 12 when the bone anchoring element 2 is not yet inserted.

As shown in FIG. 9b, the pressure element 15 is usually pre-assembled with the receiving part 4 such that U-shaped recess 6 and the V-shaped recess 17 are aligned and such that the front portion of the pin 14 is inserted into transverse bore 13 and extends into the elongate recess 19. The pin 14 also prevents rotation of the pressure element.

Referring to FIGS. 5 to 8b, the instrument 1 for assembling a polyaxial bone anchor according to a first embodiment includes a first member 30 that is configured to engage the receiving part 4 and a second member 50 that is configured to contact the head 3 of the bone anchoring element 2. The first member 30 and the second member 50 are movable with respect to each other and an indication of the relative position of the first member 30 and the second member 50 is used to provide an indication of the relative position of the bone anchor element 2 with respect to the receiving part 4. A cap member 45 may be provided that is configured to be attached to the first member 30.

The first member 30 is a hollow tubular member comprising a front end 30a and rearward end 30b and a longitudinal axis L. Adjacent to the front end 30a an engagement portion 31 for engagement with the receiving part 4 is provided. The engagement portion 31 includes an external thread that cooperates with the internal thread 8 of the receiving part 4. At a distance from the front end 30a, an abutment surface 32 is provided that abuts against the top end 4a of the receiving part 4 and thus limits the insertion of the engagement portion 31 between the legs 7a, 7b. A plurality of elongate windows 33 may be provided in the wall of the tubular first member 30. The elongate windows 33 may be arranged in the circumferential direction at equidistant intervals and may be arranged in the longitudinal direction in a line, respectively. The windows 33 may serve for observing the second member 50 inside the first member 30 and/or may reduce the amount of material for the first member 30 or lower the weight of the instrument 1. In addition, they facilitate cleaning of the instrument 1, for example, in view of improved water drainage and drying.

As shown in FIG. 8b, adjacent to the rearward end 30b of the first member 30, an internally threaded section 34 is provided for receiving the cap member 45 described below. Following the internally threaded section 34 a grip portion 35 is provided that has a greater outer diameter than the remaining parts of the first member 30. The grip portion 35 may comprise shallow longitudinal grooves 36 or any other features that facilitate gripping of the instrument with the hands. Also, longitudinally extending elongate windows 37 may be provided in the grip portion 35 that allow the inspection of the second member 50. An outer surface portion 38 between the grip portion 35 and the rearward end 30b has a smaller diameter than the grip portion 35 but a larger diameter than the remaining portions of the first member 30.

Adjacent to the internally threaded section 34, there is an accommodation space 39, an inner diameter of which is large enough so that it can accommodate a helical spring 40 therein. At a distance from the rearward end 30b the inner diameter of the passage is reduced to confine the accommodation space 39 and to form an inner shoulder 41 for abutment of the second member 50.

Figure 5:
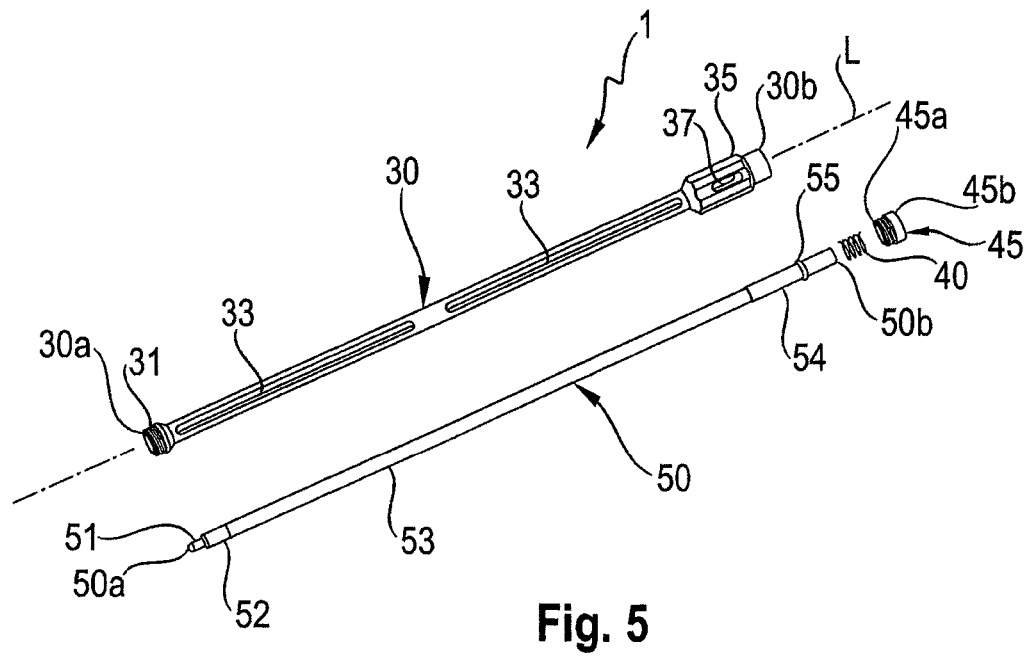
FIG. 5 shows a perspective exploded view of the instrument according to a first embodiment.
Figure 6:
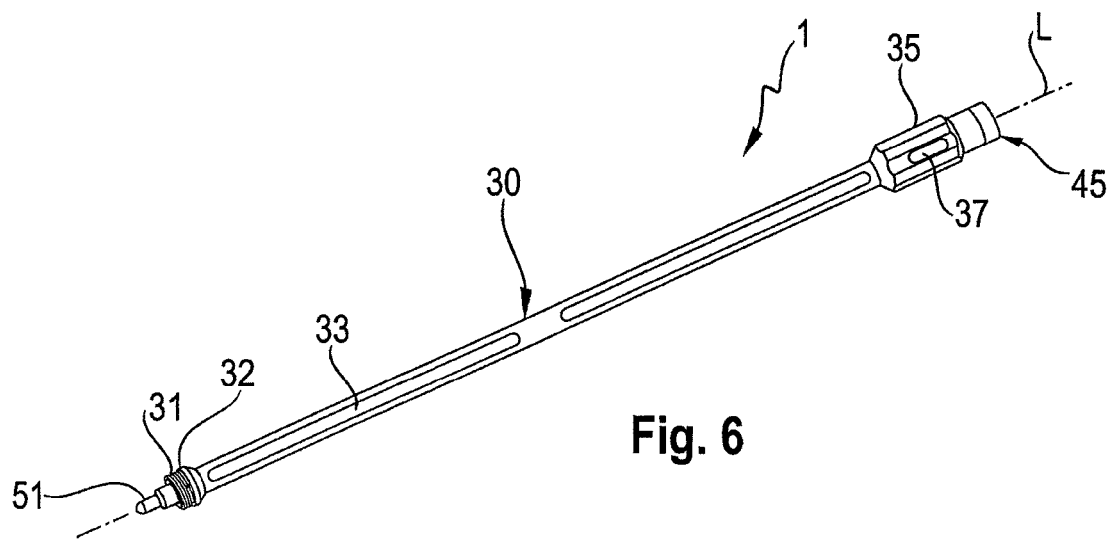
FIG. 6 shows a perspective view of the instrument of FIG. 5 in an assembled state.

The second member 50 is a substantially elongate rod and functions as a caliper. It has a front end 50a and a rearward end 50b. At the front end 50a, the second member 50 comprises a rounded tip portion 51. An outer diameter of the tip portion 51 is smaller than an inner diameter of the coaxial bore 18 of the pressure element 15 so that the tip portion 51 can extend through the coaxial bore 18 of the pressure element 15 into the cap-like section 20. Following the rounded tip portion 51, the second member 50 comprises a portion 52 with an outer diameter that is greater than the outer diameter of the tip portion 51 and smaller than the inner diameter of the first member 30 in a region adjacent to the front end 30a. The portion 52 may have a taper 52a towards the front end mating the shape of the bottom of the recess 17 of the pressure element 15. Following the portion 52 there is a middle portion 53 with a slightly smaller outer diameter so that the second member 50 has a distance from the windows 37 in this region that improves the visibility of the second member 50 and reduces a friction that may occur when the second member 50 slides in the first member 30. Adjacent to the rearward end 50b there is a fourth section 54 with an outer diameter smaller than an inner diameter of the first member 30 but larger than the outer diameter of the middle portion 53, as shown in FIG. 5. At a distance from the rearward end 50b an outwardly extending ring 55 is provided, the outer diameter of which is smaller than an inner diameter of the accommodation space 39 but greater than an inner diameter at the inner shoulder 41. By means of this, the ring 55 abuts against the inner shoulder 41 of the first member 30. The ring 55 further provides a support for the helical spring 40.

The cap member 45 has front end 45a and a rearward end 45b. Adjacent to the front end 45a, there is an externally threaded section 46 that cooperates with the internally threaded section 34 of the first member 30. Adjacent to the rearward end 45b, a cylindrical section is provided, the outer surface of which is flush with the outer surface of the portion 38 of the first member 30 when the cap member 45 is mounted to the first member 30. The cap member 45 further comprises a through bore 47 with an inner diameter that is configured to receive the end portion 54 of the second member 50. The cap member 45 may have a ring shaped recess 48 adjacent to the front end 45a to accommodate a portion of the helical spring 40 therein.

In the assembled state, the second member 50 is inserted with its rounded tip portion 51 into the first member 30 so that the ring 55 of the second member 50 abuts against the inner shoulder 41 of the first member 30. The helical spring 40 is mounted around the portion 54 and rests on the ring 55. The cap member 45 is screwed onto the rearward end 30b of the first member 30 and the spring 40 can extend into the recess 48. In this condition the spring 40 may be without force or slightly compressed to urge the ring 55 of the second member 50 towards the inner shoulder 41 of the first member 30. The rounded tip portion 51 extends outward from the front end 30a of the first member 30. As can be seen in particular in FIGS. 8a and 8b, the rearward end 50b of the second member 50 does not project out of the first member 30 when the cap member 45 is mounted, i.e., the rearward end of the second member 50 is within the through-bore 47 of the cap member 45.

The dimensions and sizes of the portions of the instrument 1 are selected such that when the surface of the rearward end 50b of the second member 50 is flush with the surface of the rearward end 45b of the cap member 45, the bone anchoring element 2 assumes a straight position and is clamped by the pressure element 15 as shown in FIGS. 15a to 16b. The position of the end surface of the second member 50 relative to the cap member 45 and therefore relative to the first member 30 acts as a position indicator.

The instrument 1 is made of a body compatible material such as a body compatible metal, for example, titanium or stainless steel or a body compatible metal alloy, such as, for example, a nickel titanium alloy, for example Nitinol. It may also be made of a body compatible plastic material, such as, for example PEEK (polyaryletheretherketone). The parts of the instrument may be made all of the same or of different materials. The material of the polyaxial bone anchor may also be a body compatible metal, metal alloy or plastic material as listed above.

Figure 10A:
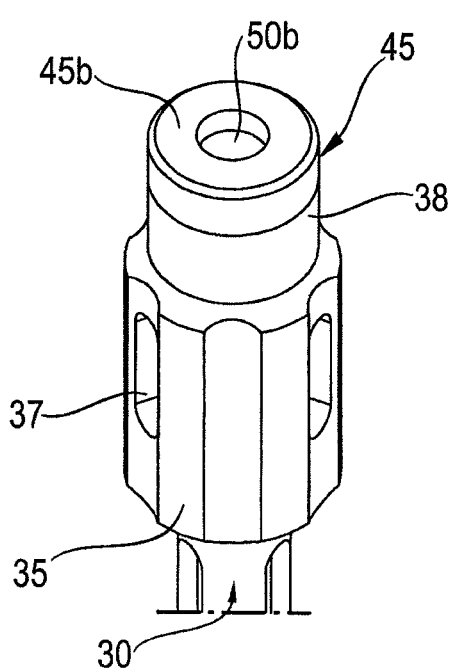
Figure 10B:
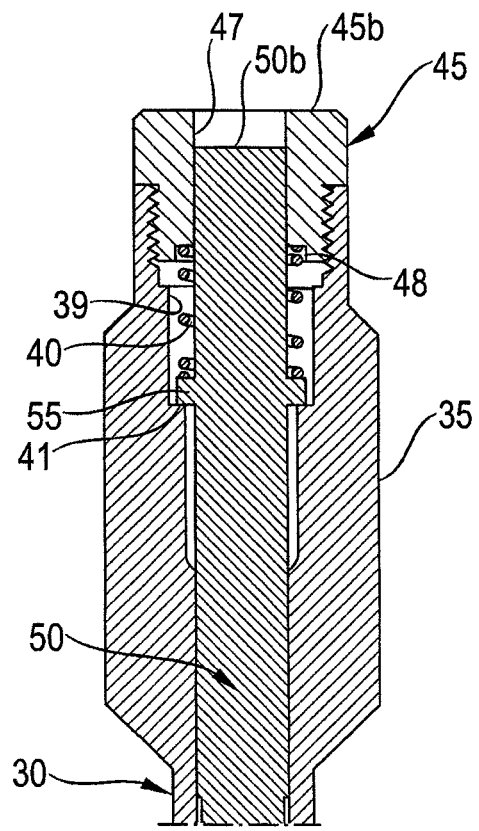

In use, first, the bone anchoring element 2 is inserted into the bone or in a vertebra, for example, into a pedicle of a vertebra 100 as shown in FIG. 1. Thereafter, the instrument 1 is attached to the receiving part 4 of the polyaxial bone anchor by screwing the engagement portion 31 between the legs 7a, 7b of the receiving part 4 until the top end 4a of the receiving part 4 abuts against the abutment surface 32 of the first member 30. As shown in FIG. 9b the pressure element 15 is arranged in the receiving part 4 and the tip portion 51 of the second member 50 extends through the coaxial bore 18 of the pressure element 15 into the cap-like portion 20. The pressure element 15 is arranged in the receiving part 4 such that the outer and inner tapered portions 22, 11 of the cap-like member 20 and the receiving part 4 still engage each other. In this condition the surface of the rearward end 50b of the second member 50 is in a lengthwise direction in a retracted position relative to the rearward surface 45 of the cap member 45 as shown in FIGS. 10a and 10b.

Figure 11A:
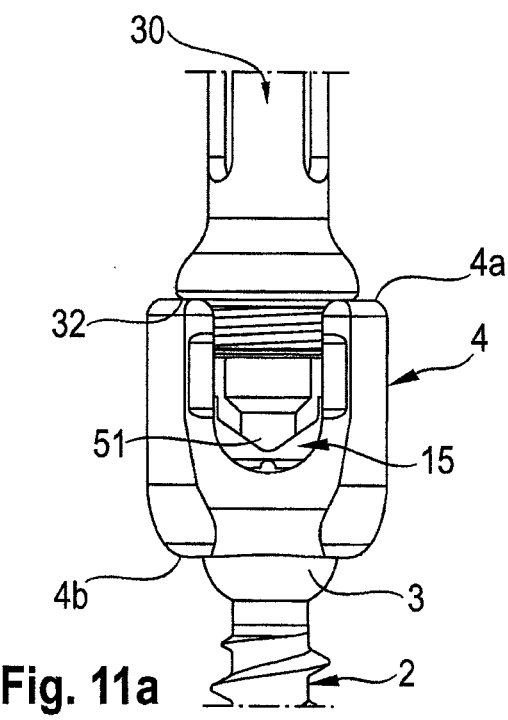
FIG. 11a shows a side view of the front end portion of the instrument attached to the receiving part with the bone anchoring element being inserted through the bottom end of the receiving part according to the first embodiment.
Figure 11B:
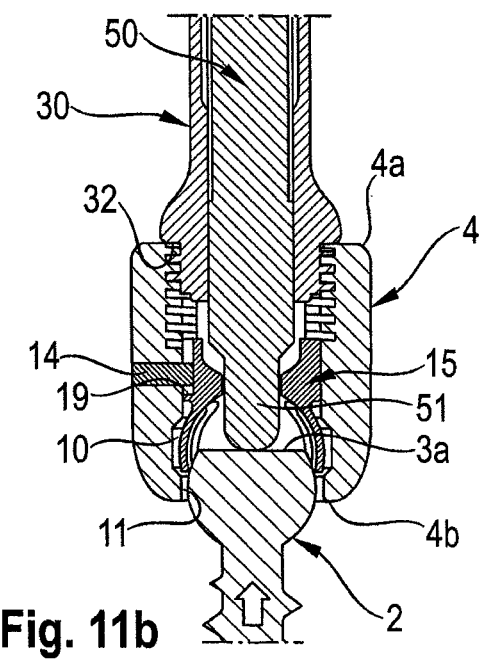
Figure 12A:
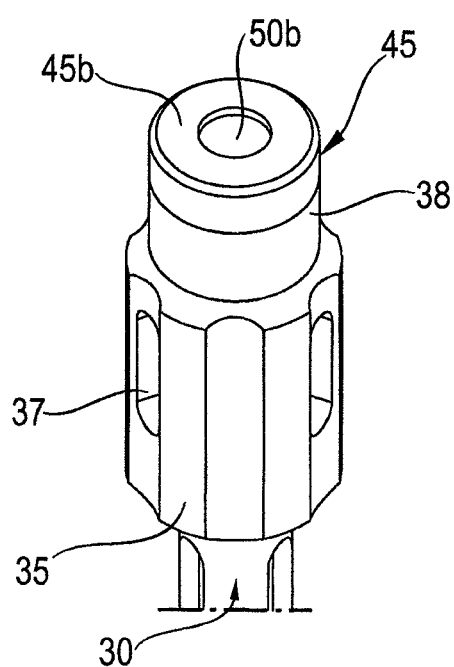
Figure 12B:
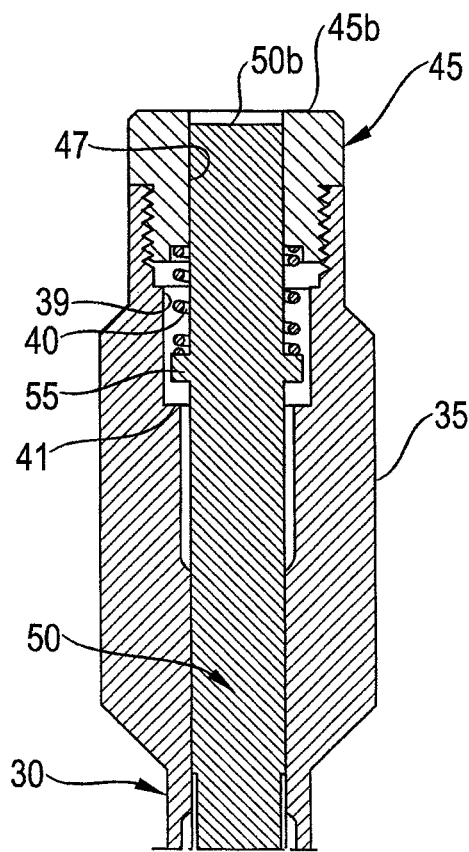
Figure 13A:
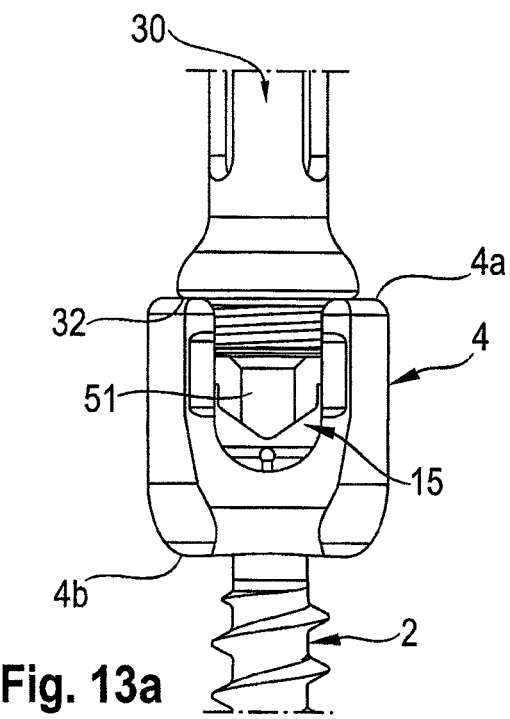
FIG. 13a shows a side of the front end portion of the instrument attached to the receiving part in which the head of the bone anchoring element has been fully introduced.
Figure 13B:
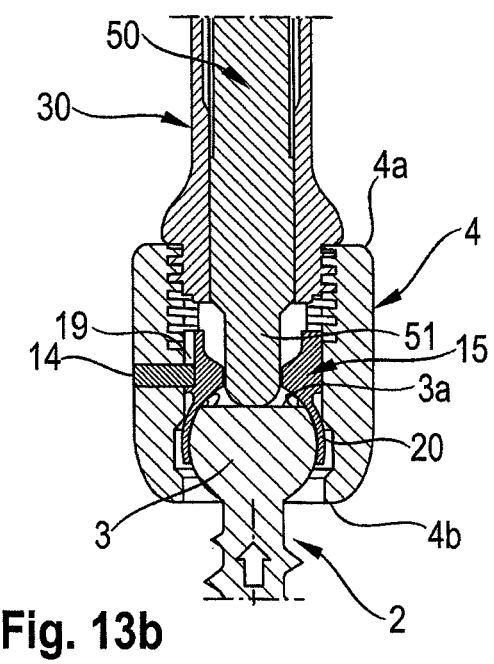

Next, as shown in FIGS. 11a to 12b, the head 3 of the anchoring element 2 is inserted through the lower opening 12 into the receiving part 4 until the free end surface 3a abuts against the rounded tip portion 51 of the second member 50, as best seen in FIG. 11b. By the introduction of the head 3, the pressure element 15 is moved upward until its bottom end 15b is above the tapered portion 11 of the receiving part 4. The free end surface 3a of the head 3 presses against the tip portion 51 and moves the second member 50 upward until the surface of the rearward end 50b is only slightly below the end surface of the rearward end 45b of the cap member 45, as can be seen in FIGS. 12a and 12b. By means of the upward movement of the second member 50 the spring 40 is compressed.

Figure 14A:
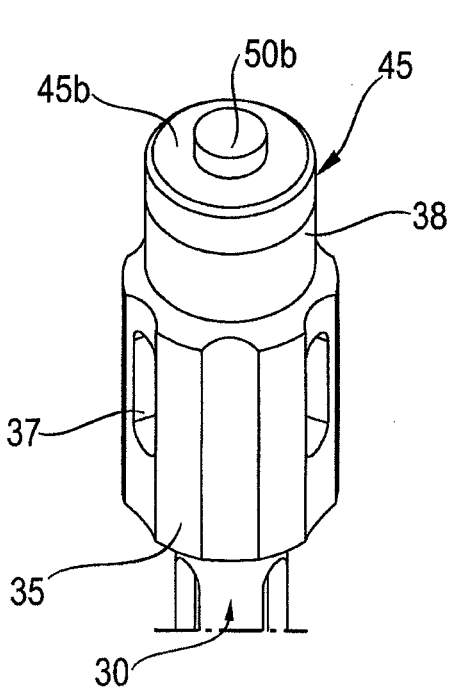
Figure 14B:
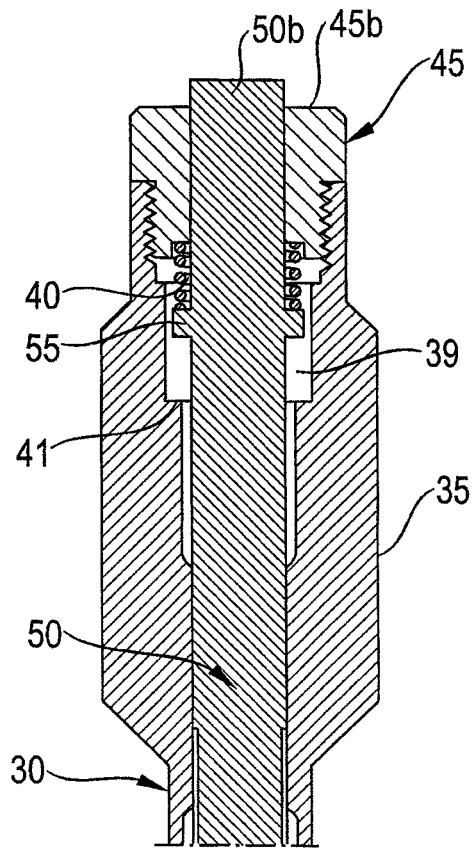

In a next step, as shown in FIGS. 13a to 14b, the receiving part 4 has been further moved downwards relative to the bone anchoring element 2 so that the head 3 is fully inserted into the receiving part 4 and the cap-like portion 20 has snapped over the head 3. Because the pressure element 15 has moved upwards relative to the receiving part 4, the flexible wall sections of the cap-like section 20 can expand into the widened region 10 of the receiving part 4 to permit the head 3 entering the cap-like portion 20. A further upward movement of the pressure element 15 is prevented by means of the pin 14 abutting against the bottom of the elongate recess 19, as can be seen in particular in FIG. 13b. The second member 50 has moved upward so that its rearward end 50b projects out of the cap 45, as can be seen in FIGS. 14a and 14b. In this condition, the spring 40 is further compressed.

In a next step, shown in FIGS. 15a to 16b, the instrument 1 is slightly drawn upward so that, relative to the pressure element 15 which stays in place, the tapered outer surface portion 22 of the cap-like portion 20 is drawn into tapered portion 11 of the receiving part 4 in order to clamp the head 3. The second member 50 follows the downward movement of the head 3 because it is urged by means of the spring 40 downward and the end surfaces are 45b, 50b of the cap 45 and the second member 50, respectively, are flush with each other as shown in FIGS. 16a and 16b. The bone anchoring element 2 assumes an angle of 0° with respect to the central axis C and is correctly mounted. Hence, the correct position in the clamped state with 0° pivot angle is indicated by an even surface of the rearward end 45b, 50b of the instrument 1. Such even surface can be easily recognized by the eyes or felt with the thumb of a user in order to determine whether the position of the receiving part 4 relative to the anchoring element 2 is correct.

Figure 17A:
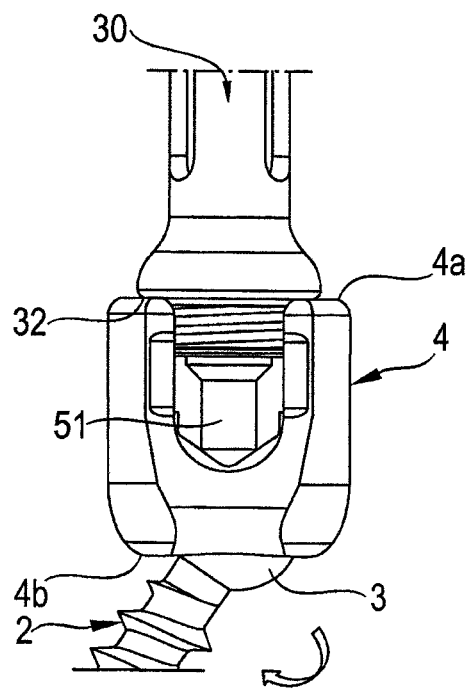
FIG. 17a shows a side view of the front end portion of the instrument attached to the receiving part wherein the bone anchoring element has been pivoted to one side according to the first embodiment.
Figure 17B:
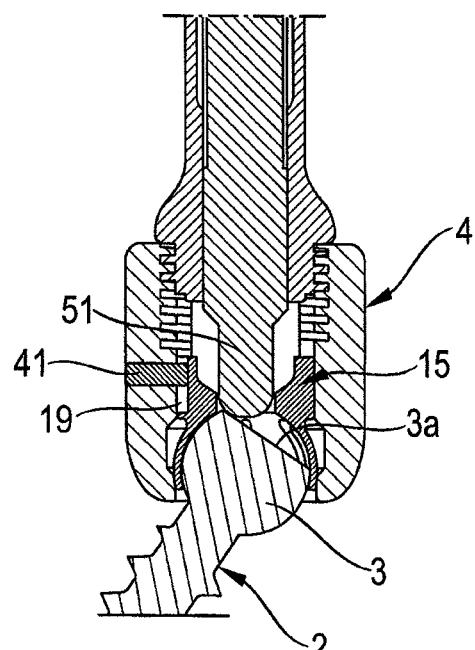
Figure 18A:
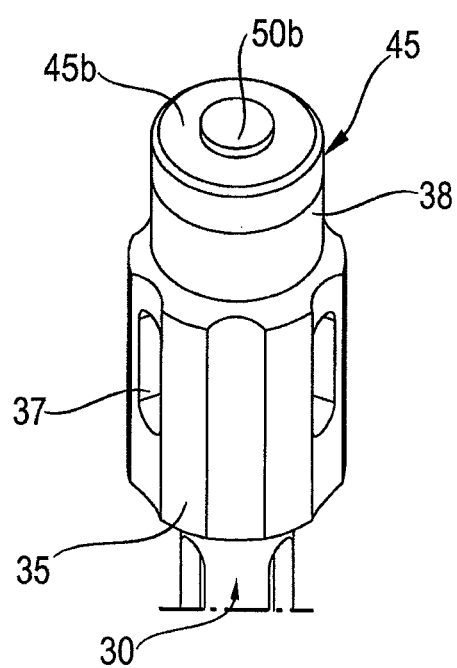
Figure 18B:
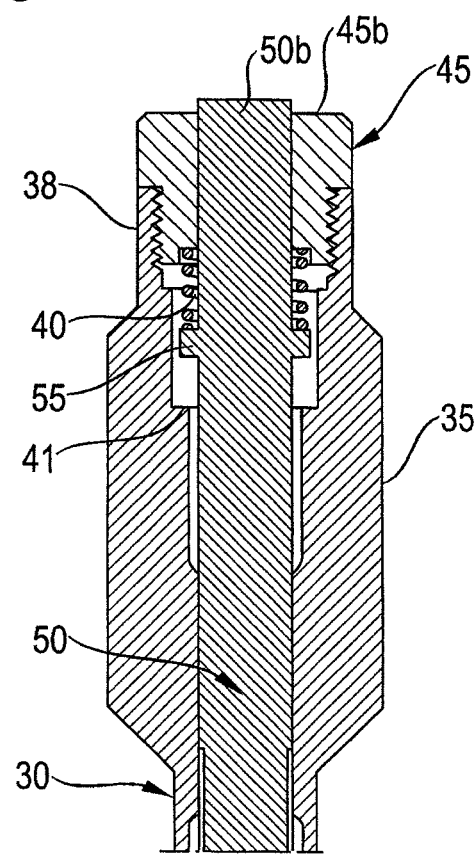

Next, when the correctly mounted position is achieved in which the head 3 is clamped by the pressure element, the receiving part 4 is pivoted with respect to the bone anchoring element 2 so that the bone anchoring element 2 and the receiving part 4 assume an angle with each other shown in FIGS. 17a and 17b. The free end surface 3a of the head 3 pushes the rounded tip portion 51 of the second member 50 upward so that the second member 50 is moving upward until it slightly protrudes over the end surface 45b of the cap member 45 as shown in FIGS. 18a to 18b.

Hence, the indication of the position of the bone anchoring element 2 relative to the receiving part 4 is twofold. An even upper surface, i. e. when the end surface 50b of the second member 50 is flush with the end surface 45b of the cap 45, indicates that a bone anchoring element 2 is in the clamped position with a pivot angle of 0°. Starting from this position, any pivot angle in the correctly mounted state can be indicated by the height to which the end surface 50b of the second member 50 protruding outward from the end surface 45b of the cap member 45.

In a modification of the first embodiment the rearward end surfaces 45b of the cap 45 and the second member 50 are coloured with different colours to enhance the visibility of the height differences between them. In a further modification, the end portion 50b of the second member 50 may have a scale, for example, an engraved scale, that indicates a pivot angle of the bone anchoring element 2 relative to the receiving part 4 starting from the 0° position.

Referring now to FIGS. 19 to 20b, a second embodiment 1' includes first member 30' a second member 50' and a third member 60'. The first member 30' is designed like the first member 30 of the first embodiment. The inner diameters of the passages in the first member 30' may be adapted to receive a second member 50' and a third member 60'. Parts and portions that have identical or similar shape to that of the first embodiment are indicated with the same reference numerals and the description thereof will not be repeated. The second member 50' is a rod-shaped element that has a substantially constant diameter. A rounded tip portion 51' is provided at the front end 50a. At a distance from the rearward end 50b, a transverse hole 57 is provided for receiving a pin 58 for connecting the second member 50' to the third member 60' and for guiding the third member 60' together with the second member 50'. The third member 60' is a tube-shaped member with a front end 60a and a rearward end 60b. Adjacent to the front end 60a, there is a first portion 61 with an outer diameter that mates with the inner diameter of the first member 30' at the engagement portion 31. The first portion 61 tapers towards the front end 60a in a tapered section 61a such that there is a contact area between the tapered portions 61a of the first portion 61 and the bottom V-shaped recess 17 of the pressure element 15.

As can be further seen in FIG. 19, the third member 60' has adjacent to the first portion 61 a middle portion 62 with a reduced diameter and an end portion 63 with a greater diameter compared to the middle portion 62. At a distance from the rearward end 62b, there is an outwardly extending ring 65 on which a first helical spring 40' can rest when it is mounted from the rearward end 60b.

In the end portion 63, at a distance from the ring 65, elongate through-holes 64 are provided extending through the tubular member 60' in a transverse direction. The elongate through-holes 64 are elongate in the axial direction and receive the pin 58, when the second member 50' is in the third member 60'. The length of the pin 58 is slightly smaller than the inner diameter of the accommodation space 39' of the first member 30'. Between the pin 58 and the ring 65, a second helical spring 40" is provided that rests on a washer 42 provided between the ring 65 and the pin 58. The cap 45 is identical to the cap 45 of the first embodiment.

Hence, as can be seen in particular in FIG. 20b the third member 60' is biased via the two springs 40', 40" with respect to the first member 30'. The second member 50' is guided via the pin 58 extending through the elongate transverse holes 64 in the third member 60'.

The sizes of the members are such that, as shown in FIGS. 20a and 20b when the third member 60' is in its lower position with respect to the first member 30', the pin 58 is arranged at the bottom of the elongate transverse holes 64 in the direction of the front end 30a and the end surfaces 60b, 50b of the third member 60' and the second member 50' are retracted with respect to the end surface 45b of the cap 45. In this condition, the first portion 61 of the third member and the rounded tip portion 51' of the first member 30' protrude outward from the front end 30a of the first member 30'. Furthermore, the rounded tip portion 51' protrudes out of the front end 60a of the third member 60'.

Figure 21A:
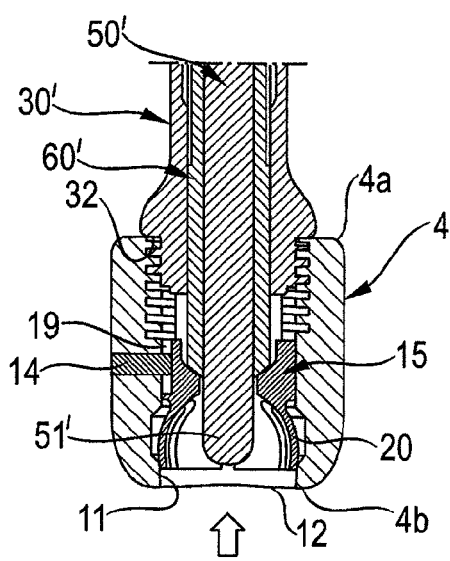
FIG. 21a shows a cross-sectional view of the front end portion of the instrument according to the second embodiment attached to the receiving part.
Figure 21B:
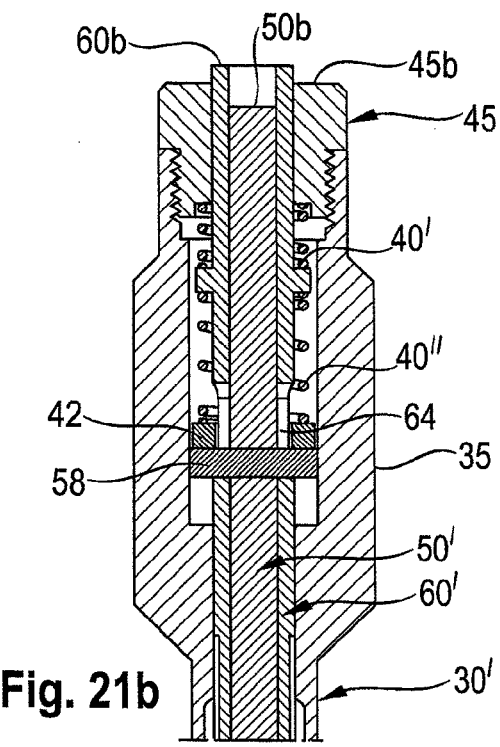

In use, first, the instrument 1' is attached to the receiving part 4 as shown in FIGS. 21a and 21b. Thereby, the rounded tip portion 51' extends through the coaxial through-hole 18 of the pressure element 15 into the inside of the cap-like portion 20 of the pressure element 15 until the tapered end portion 61a of the third member 60' rests on the bottom of the V-shaped recess 17 of the pressure element 15, as shown in FIG. 21a. At the same time, the third member 60' and the second member 50' are moved upward by compressing the first spring 40' between the ring 65 and the recess 48 of the cap member 45. The end surface of the rearward end 60b slightly protrudes outward from the end surface of the rearward end 45b of the cap member 45, as shown in FIG. 21b.

Figure 22A:
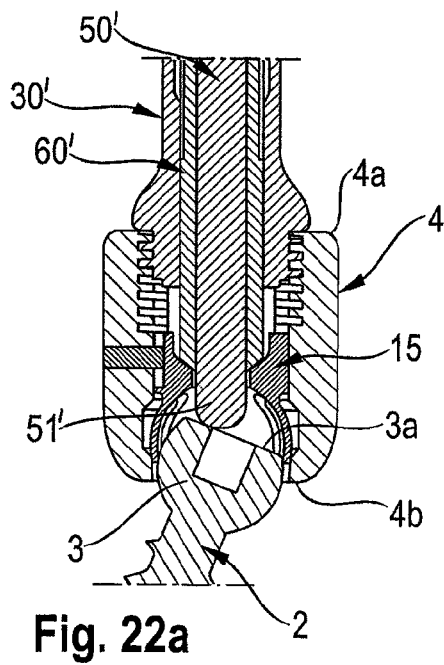
FIG. 22a shows a cross-sectional view of the front end portion of the instrument attached to the receiving part wherein the bone anchoring element is inserted from the bottom end according to the second embodiment.
Figure 22B:
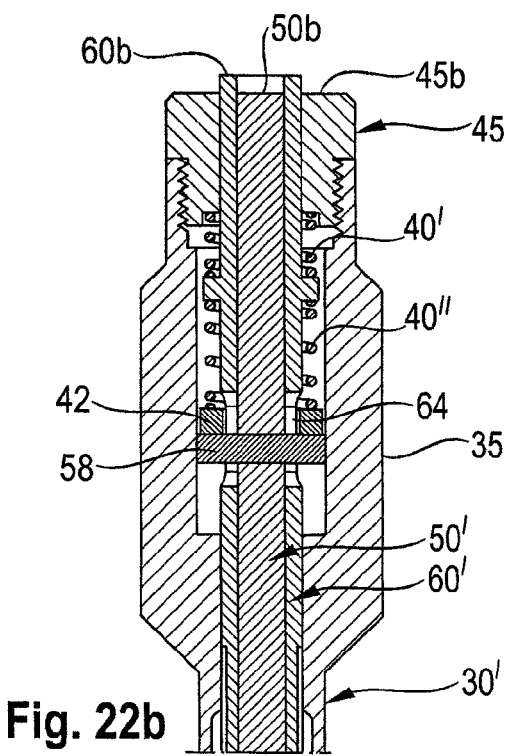

In a next step, when the head 3 of the bone anchoring element 2 is inserted through the lower opening 12 of the receiving part 4, the head 3 moves the rounded tip portion 51' slightly upwards thereby also moving the pin 58 upward as shown in FIGS. 22a and 22b. Hence, the third member 60' and the second member 50' move upward together.

Figure 23A:
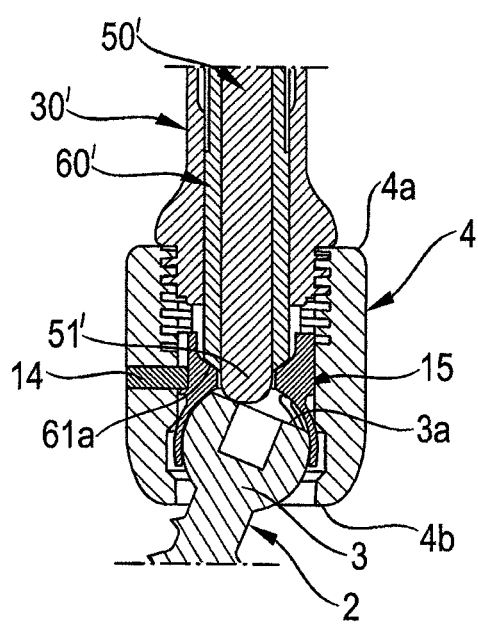
FIG. 23a shows a cross-sectional view of the front end portion of the instrument according to the second embodiment that is attached to the receiving part with the head of the bone anchoring element fully inserted.
Figure 23B:
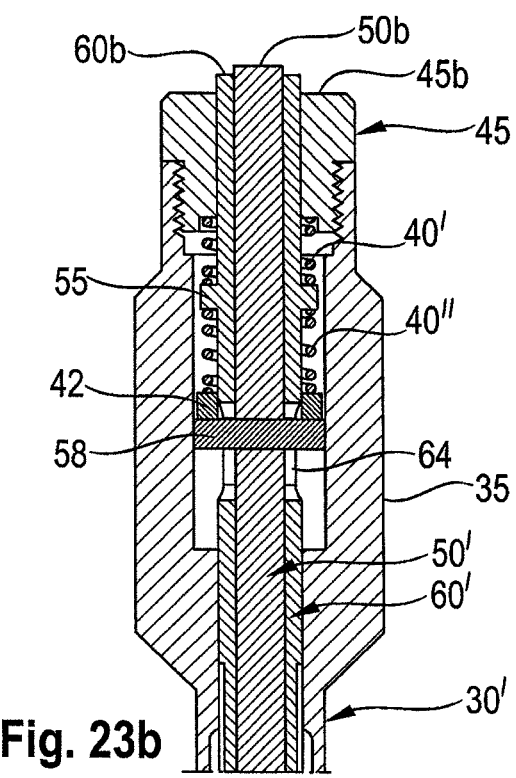

Next, as shown in FIGS. 23a and 23b, the receiving part 4 is fully mounted onto the head 3 of the bone anchoring element 2 and the pressure member 15 is moved upward until the pin 14 abuts against the bottom of the elongate recess 19. In this condition, the pin 58 has moved upward together with the second member 50' until it abuts against the upper rim of the elongate transverse holes 64. Both springs 40', 40" are compressed and both ends of the second and the third member 50b, 60b protrude out of the surface of the rearward end 45b of the cap 45.

Figure 24A:
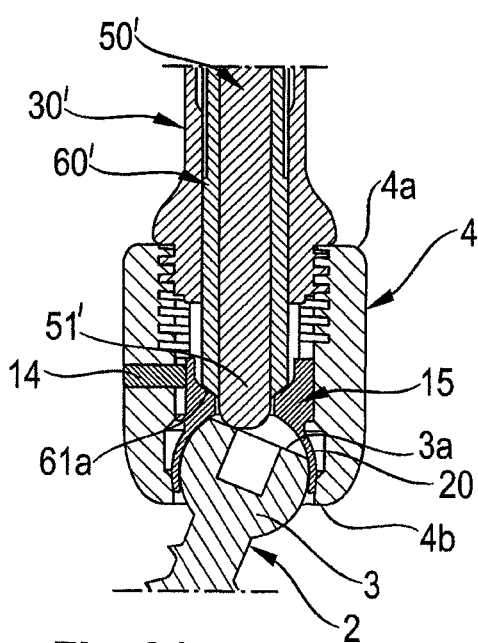
FIG. 24a shows a cross-sectional view of the front end portion of the instrument attached to the receiving part with the head of the bone anchoring element clamped in the receiving part according to the second embodiment.
Figure 24B:
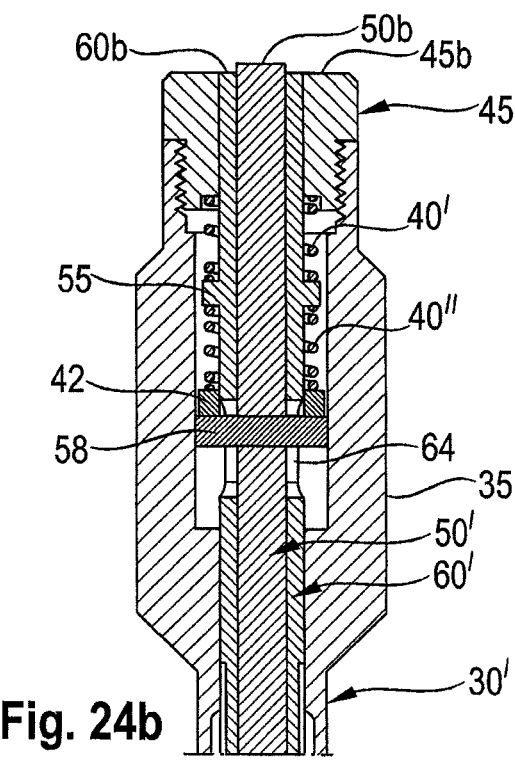

Thereafter as shown in FIGS. 24a and 24b, the receiving part 4 is slightly drawn upward with the instrument until the cap-like portion 20 is pressed into the tapered portion 11 of the receiving part 4 and clamps the head. The position of the rearward end surface of the third member 60' is flush with the end surface of the cap 45 and indicates a correct position of the pressure element 15. The end surface 50b of the second member 50' still protrudes slightly over the end surfaces 60b, 45b of the third member 60' and the cap 45.

The position indicator of the second embodiment is realized by the position of the end surface 60b of the third member 60' relative to the end surface 45b of the cap member 45. When they are flush with each other, the position of the pressure element 15 and also of the head 3 relative to the receiving part 4 is correct.

Figures 25A, 25B, 25C:
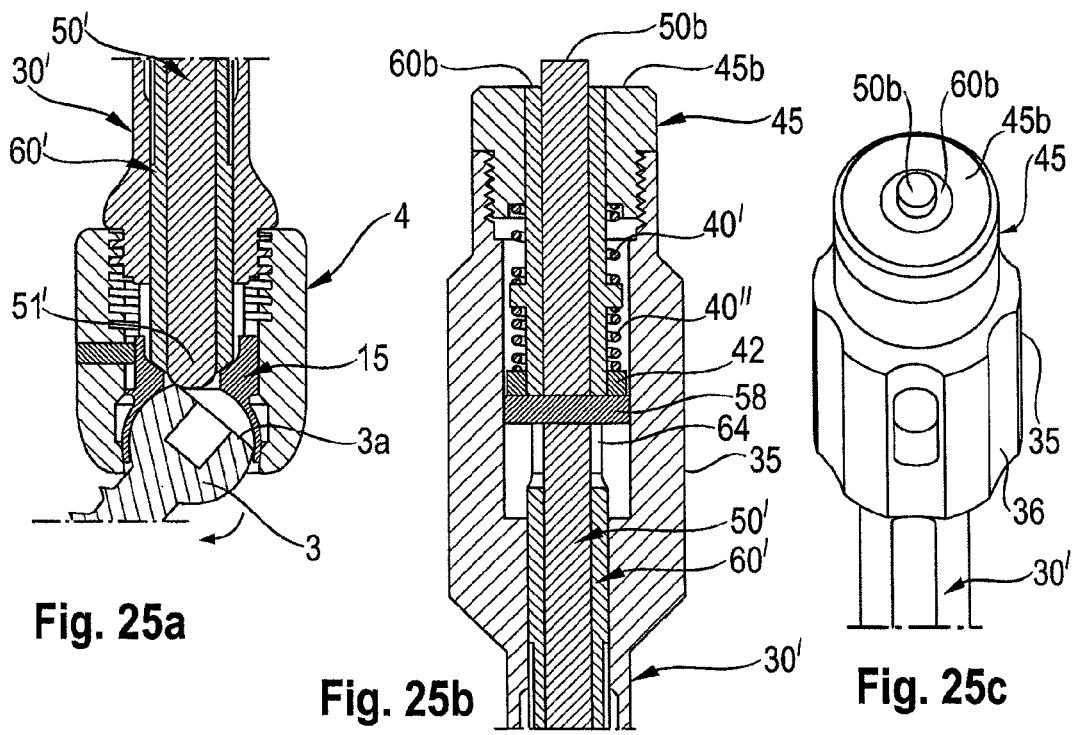

Finally, the receiving part 4 is pivoted so that it assumes an angular position with respect to the bone anchoring element 2. This further moves the second member 50' up while the third member 60' remains at its position. Hence, as shown in FIGS. 25b and 25c, the user can recognize that the pressure element 15 is correctly positioned because the end surface 60b of the third member 60' and the end surface 45b of the cap 45 are flush with each other. Furthermore, the degree of angulation can be recognized by inspecting the height of the protrusion of the second member 50' which can be recognized with respect to the even surface of the ends 60b, 45b of the third member 60' and the cap 45.

Also in this embodiment, the end surfaces 45b, 50b, 60b may have different colours to facilitate the recognition of their relative positions with respect to each other. Also, the 50b, 60b end portions of the second member 50' and the third member 60' may have a scale that indicates, for example, the pivot angle.

Figure 26:
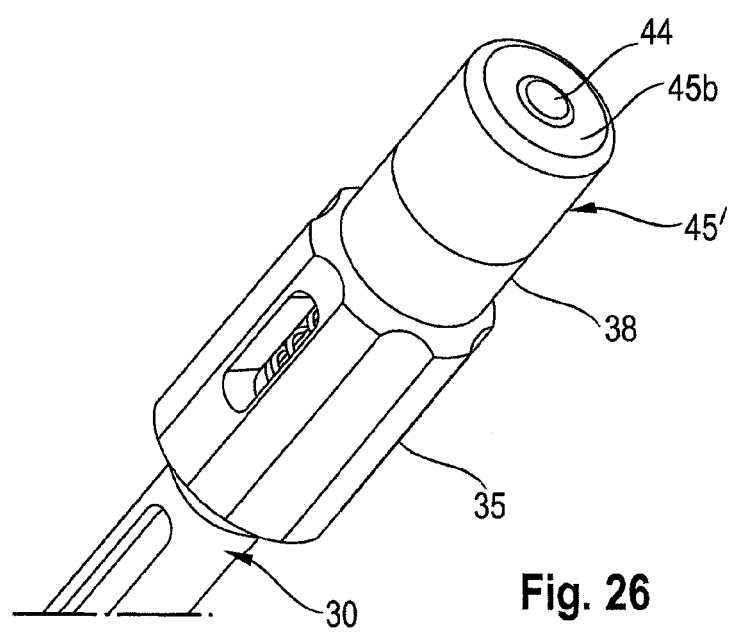
FIG. 26 shows a rear end portion of the instrument according to a third embodiment.

A third embodiment will be briefly explained with reference to FIG. 26. FIG. 26, the cap 45' is sized larger than in the previous embodiments and comprises a window 44 with an optical or electro-optical indication device. Inside the cap 45' is a larger accommodation space that may accommodate detection devices such as sensors or switches or any other detection device that detect the relative position of the first member 30, 30' and the second member 50, 50' and, if a third member 60' is present, also of the third member 60' relative to first member 30, 30' and the second member 50, 50'. The relative position may be indicated optically or acoustically. For an optical or electro-optical indication, for example, LEDs can be used. For an acoustic detection, for example a certain sound or even a voice indication may be conceivable.

It shall be noted that the invention can also be realised through other ways. For example, instead of a relative longitudinal position of the members with respect to each other, a relative rotational position could be detected that is indicative of the relative position of the bone anchoring element with respect to receiving part.

While the embodiments show a cap member which is connected to the first member, the cap can also be omitted and the first member designed so as to fulfil the function of the cap member.

Instead of the helical springs, other kinds of springs can be used.

The polyaxial bone anchoring device can be designed differently. In particular, the invention is not limited to a bottom loading type polyaxial bone anchor but can also be used with a top loading polyaxial bone anchor wherein the bone anchoring element is inserted from the top end 4a of the receiving part 4. Other devices than the pin for preventing rotation of the pressure element and for providing a stop against escaping of the pressure element may be provided.

With respect to the polyaxial bone anchor, other kinds of locking devices, including outer nuts, outer caps, bayonet locking devices, or others are also possible. Also, a two part locking device may be used with an outer locking device that acts onto the pressure element only and an inner locking device that presses onto the rod.

For the bone anchoring element, various different kinds of anchoring elements can be used and combined with the receiving part. These anchoring elements may be, for example, screws with different lengths, screws with different diameters, canulated screws with different thread forms, nails, hooks etc.

It shall also be noted that portions of the described embodiments can also be combined with each other in various different combinations.

The invention claimed is:

1. An instrument for assembling a polyaxial bone anchor, the polyaxial bone anchor comprising a bone anchoring element having a head and a shank and a receiving part configured to pivotably receive the head of the bone anchoring element, the instrument comprising:
   a first member having a front end and a rearward end, the front end having a threaded engagement portion configured to releasably attach to the polyaxial bone anchor;
   a second member having a front portion and a rearward end, the front portion comprising a front end having a tip, wherein the second member is insertable into the first member;
   a position indicator located at a position away from the front portion of the second member and configured to indicate a distance between the front portion of the second member and the front end of the first member when the second member is inserted into the first member; and
   a spring configured to bias the front portion of the second member to protrude from the front end of the first member when the second member is inserted into the first member; and
   wherein the front portion of the second member is movable with respect to the front end of the first member when the second member is inserted into the first member.

2. The instrument of claim 1, wherein the first member is an elongate hollow member with a longitudinal axis and the second member is an elongate member configured to extend at least partially through the first member.

3. The instrument of claim 1, wherein the second member is configured to move within the first member in an axial direction.

4. The instrument of claim 1, wherein the first member comprises a cap member, wherein the position indicator comprises the rearward end of the second member and the cap member, and wherein when the cap member is fully seated onto the first member, the front portion of the second member is movable with respect to the front end of the first member.

5. The instrument of claim 4, wherein the cap member comprises a threaded section to mount to the first member and the first member comprises a threaded section to engage the cap member, and wherein when the cap member is fully threaded onto the first member, the front portion of the second member is movable with respect to the front end of the first member.

6. The instrument of claim 1, wherein the engagement portion of the first member is configured to engage the receiving part of the polyaxial bone anchor and wherein the tip of the second member is configured to contact the head of the bone anchoring element.

7. The instrument of claim 6, wherein, when the second member is inserted into the first member and the engagement portion is engaging the receiving part, the spring is biased such that the second member follows movement of the head when the tip of the second member is in contact with the head.

8. The instrument of claim 6, wherein the polyaxial bone anchor further comprises a pressure element configured to exert pressure onto the bone anchoring element to lock the bone anchoring element in an angular position and wherein the second member further comprises a third member configured to contact the pressure element.

9. The instrument of claim 8, wherein the position indicator is further configured to indicate the position of the pressure element relative to the receiving part based on the position of the third member relative to the first member.

10. The instrument of claim 8, wherein the third member comprises a front end configured to contact the pressure element and a rearward end, and wherein the position indicator comprises the rearward end of the third member.

11. The instrument of claim 8, wherein the second member further comprises a central portion and the third member is biased against the central portion of the second member by a second spring.

12. The instrument of claim 11, wherein movement of the central portion of the second member relative to the third member is limited by at least one stop.

13. The instrument of claim 6, wherein the position indicator is configured to indicate a correct position of the bone anchoring element relative to the receiving part by two surfaces that are flush with each other.

14. The instrument of claim 1, wherein the position indicator includes the rearward end of the second member.

15. The instrument of claim 1, wherein the first member comprises an abutment configured to engage the polyaxial bone anchor to limit insertion of the threaded engagement portion of the first member into the polyaxial bone anchor, the abutment having a width greater than a root diameter of the threaded engagement portion, and wherein the abutment is located between the threaded engagement portion and the rearward end of the first member.

16. The instrument of claim 15, wherein the abutment of the first member has a width greater than a largest diameter of the threaded engagement portion.

17. The instrument of claim 15, wherein the first member comprises an axis extending through the front end and the rearward end, and when the instrument is in position to be releasably attached to the polyaxial bone anchor, the abutment of the first member is located at a fixed axial position relative to the front end of the first member.

18. A method for assembling a polyaxial bone anchor using an instrument, the polyaxial bone anchor comprising a receiving part and a bone anchoring element having a head and a shank; and the instrument comprising a first member having a front end and a rearward end, the front end having a threaded engagement portion configured to releasably attach to the polyaxial bone anchor, a second member having a front portion and a rearward end, the front portion comprising a front end having a tip, a position indicator located at a position away from the front portion of the second member; and a spring, wherein the front portion of the second member is movable with respect to the front end of the first member when the second member is inserted into the first member, the method comprising:
- inserting the shank of the bone anchoring element into the bone;
- inserting the second member into the first member;
- biasing with the spring the front portion of the second member to protrude from the front end of the first member;
- attaching the receiving part with the engagement portion of the first member;
- receiving the head of the bone anchoring member into the receiving part such that the head is pivotable within the receiving part;
- contacting the head of the bone anchoring element with the tip of the second member;
- indicating a position of the head of the bone anchoring element relative to the receiving part based on a distance between the front portion of the second member and the front end of the first member.

19. An instrument for assembling a polyaxial bone anchor, the instrument comprising:
- a first member having a front end and a rear end, the front end having an engagement portion;
- a second member having a front portion and a rearward end, the front portion comprising a front end having a tip, wherein the second member is insertable into the first member;
- a cap member having a front end, a rear end, and a shoulder to abut against the rear end of the first member;
- a position indicator located at a position away from the front portion of the second member and configured to indicate a distance between the front portion of the second member and the front end of the first member when the second member is inserted into the first member; and
- a spring configured to bias the front portion of the second member to protrude from the front end of the first member when the second member is inserted into the first member;
- wherein the front portion of the second member is movable with respect to the front end of the first member when the second member is inserted into the first member; and
- wherein in a first configuration when the second member is inserted into the first member and the shoulder of the cap member abuts against the rear end of the first member, the rearward end of the second member is retracted relative to the rear end of the cap member, and
- wherein in a second configuration when the second member is inserted into the first member, when the shoulder of the cap member abuts against the rear end of the first member, and when the tip of the second member projects from the front end of the first member, the rearward end of the second member projects out of the rear end of the first member.

20. The instrument of claim 19, wherein in a third configuration when the second member is inserted into the first member and the shoulder of the cap member abuts against the rear end of the first member, the rearward end of the second member is flush with the rear end of the cap member.

21. An instrument for assembling a polyaxial bone anchor, the polyaxial bone anchor comprising a bone anchoring element having a head and a shank and a receiving part configured to pivotably receive the head of the bone anchoring element, the instrument comprising:
- a first member comprising a front end, a rearward end, and a tubular body defining a cavity extending between the front end and the rearward end, the tubular body having a wall with one or more elongate openings extending through the wall into the cavity, the front end having an engagement portion configured to releasably attach to the polyaxial bone anchor;
- a second member having a front portion and a rearward end, the front portion comprising a front end having a tip, wherein the second member is insertable into the first member;
- a position indicator located at a position away from the front portion of the second member and configured to indicate a distance between the front portion of the second member and the front end of the first member when the second member is inserted into the first member; and
- a spring configured to bias the front portion of the second member to protrude from the front end of the first member when the second member is inserted into the first member;
- wherein the front portion of the second member is movable with respect to the front end of the first member when the second member is inserted into the first member; and
- wherein when the front portion of the second member protrudes from the front end of the first member, the one or more elongate openings of the first member are positioned entirely between the front end of the first member and a front end of the spring.

22. The instrument of claim 21, wherein the first member further comprises a plurality of elongate openings.

* * * * *

UNITED STATES PATENT AND TRADEMARK OFFICE
CERTIFICATE OF CORRECTION

PATENT NO. : 9,517,092 B2  Page 1 of 1
APPLICATION NO. : 14/049099
DATED : December 13, 2016
INVENTOR(S) : Lutz Biedermann et al.

It is certified that error appears in the above-identified patent and that said Letters Patent is hereby corrected as shown below:

On the Title Page

(72) Inventors:            Delete "Weiswell (DE)",
Wilfried Matthis           Insert --Weisweil (DE)--

Signed and Sealed this
Twenty-fifth Day of July, 2017

Joseph Matal
*Performing the Functions and Duties of the
Under Secretary of Commerce for Intellectual Property and
Director of the United States Patent and Trademark Office*